United States Patent
Chang et al.

(10) Patent No.: US 6,468,989 B1
(45) Date of Patent: Oct. 22, 2002

(54) GEL COMPOSITIONS CONTAINING METRONIDAZOLE

(75) Inventors: Yunik Chang, Sonoma, CA (US); Gordon J. Dow, Santa Rosa, CA (US); Arturo Angel, Santa Rosa, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 25 days.

(21) Appl. No.: 09/615,169

(22) Filed: Jul. 13, 2000

(51) Int. Cl.$^7$ .................. A01N 43/04; A61K 31/715

(52) U.S. Cl. .................. 514/58; 514/23; 514/25; 514/54; 514/58; 536/1.11; 536/102; 536/103

(58) Field of Search .................. 514/23, 25, 54, 514/58; 536/1.11, 102, 103

(56) References Cited

U.S. PATENT DOCUMENTS

| | | | |
|---|---|---|---|
| 4,032,645 A | | 6/1977 | Chien et al. |
| 4,596,795 A | | 6/1986 | Pitha |
| 4,727,064 A | | 2/1988 | Pitha |
| 4,837,378 A | * | 6/1989 | Borgman ............ 424/81 |
| 5,324,718 A | * | 6/1994 | Loftsson ............ 514/58 |
| 5,472,954 A | | 12/1995 | Loftsson |
| 5,536,743 A | | 7/1996 | Borgman |
| 5,747,341 A | * | 5/1998 | Brothers ............ 435/404 |
| 5,849,776 A | | 12/1998 | Czernielewski |
| 5,928,942 A | * | 7/1999 | Brothers ............ 735/347 |
| 6,183,766 B1 | * | 2/2001 | Sine et al. ............ 424/405 |

FOREIGN PATENT DOCUMENTS

| | | |
|---|---|---|
| EP | 0 149 197 | 3/1990 |
| EP | 0 472 327 A1 | 8/1991 |
| EP | 0 335 545 B1 | 6/1993 |
| WO | WO 85/02767 | 7/1985 |
| WO | WO 90/03784 | 4/1990 |
| WO | WO 91/11172 | 8/1991 |
| WO | WO 94/02518 | 2/1994 |

OTHER PUBLICATIONS

Uekama, K, and Otagiri, M, Cyclodextrins in Drug Carrier Systems, CRC Critical Review in Therapeutic Drug Carrier Systems, vol. 3(1):1–40 (1987).

Chien, Yw, Solubilization of Metronidazole by Water–miscible Multi–cosolvents and Water–soluble Vitamins, Journal of Parenteral Science and Technology, vol. 38(1):32–36 (1984).

Giordano, F., et al., Preparation and Characterization of Metronidazole Benzoate–Gammacyclodextrin Inclusion Compound, Boll. Chim. Farmaceutico, vol. 131(4):150–156 (1992).

Andersen, FM, and Bundgaard, H, Inclusion complexation of metronidazole benzoate with β–cyclodextrin and its depression of anhydrate–hydrate transition in aqueous suspensions, International Journal of Pharmaceutics, vol. 19:189–197 (1984).

Skiba, M., et al., Development of a new colloidal drug carrier from chemically–modified cyclodextrins: nanospheres and infulence of physicochemical and technological factors on particle size, International Journal of Pharmaceutics, vol. 129:113–121 (1996).

Kata, M., and Kedvessy, G., Increasing the solubility characteristics of Pharmaca with cyclodextrins, Pharm. Ind., vol. 49:98–100 (1987).

Kata, M., and Antal, A., Production and Investigation of products containing metronidazole and β–cyclodextrin, Acta Pharmaceutica Hungarica, 54:116–122 (1984).

Hadi, Ia al, Formulation factors and physical properties of metronidazole benzoate tablets containing mixtures of β–cyclodextrins and its derivatives, Congr. Int. Tech. Pharm., 6th, 5:401–407 (1992).

European Phamacopoeia, pp. 980–981 (1995).

Physicians Desk Reference, 53 Edition, pp. 912–913 (1999).

Szejtli, J., *Cyclodextrins in Drug Formulations: Part 1*, Pharmaceutical Technology International, vol. 3(2):15–22 (1991).

Szejtli, J., *Cyclodextrins in Drug Formulations: Part 2* Pharmaceutical Technology International, vol. 3(3):16–24 (1991).

Lofftson et al., 2–Hydroxypropyl–β–cyclodextrin: Properties and Usage in Pharmaceautical Formulations, Phar. Ztg. Wiss., vol. 4/13:5–10 (1991).

Hirayama et al., in Cyclodextrins and their Industrial Uses, ed. D. Duchene, Editions de Sante, Paris, 1987, pp. 133–172.

Hassan et al., Improvement of the in vitro dissolution characteristics of famotidine by inclusion in βcyclodextrin, International Journal of Pharmaceutics, 58:19–24 (1990.

Loftsson, T., and Bodor, N., Effects of 2–hydroxypropyl–β–cyclodextrin on the aqueous solubility of drugs and transderman delivery of 17 βestradiol, Acta. Pharm. Nord., 1(4):185–193 (1989).

Pagington, J.S., β–Cyclodextrin: the success of molecular inclusion, Chemistry in Britain, pp. 455–458 (May 1987).

Loftsson, T., et al., The effects of cyclodextrin on transdermal delivery of drugs, European J. Pharm. Biopharm., 37(1):30–33 (1991).

* cited by examiner

Primary Examiner—James O. Wilson
Assistant Examiner—Patrick Lewis
(74) Attorney, Agent, or Firm—Howard Eisenberg, Esq

(57) ABSTRACT

An aqueous solution of metronidazole in which the concentration of metronidazole is higher than 0.75%. The solution contains the solubility enhancer hydroxypropyl-betacyclodextrin and may additionally contain niacinamide. Methods of manufacture and therapeutic use of the solution are disclosed.

28 Claims, 2 Drawing Sheets

GEL COMPOSITIONS CONTAINING METRONIDAZOLE

The invention pertains to the field of topically applied medications for treatment of skin and mucosal disorders. In particular, the invention pertains to aqueous gel compositions containing metronidazole as the active ingredient.

BACKGROUND OF THE INVENTION

Metronidazole, 1-(2-hydroxyethyl)-2-methyl-5-nitroimidazole, has long been known as an effective drug to treat a variety of disorders, and is especially well known for the treatment of various protozoal diseases. As a topical therapy, metronidazole has also been shown to be useful in treating various skin disorders, including acne rosacea, bacterial ulcers, and perioral dermatitis. See, Borgman, U.S. Pat. No. 4,837,378. Metronidazole has been found to have an anti-inflammatory activity when used topically to treat dermatologic disorders. See, Czernielewski, et al., U.S. Pat. No. 5,849,776. Metronidazole may also be used as an intravaginal therapeutic agent for the treatment of bacterial vaginosis. See, Borgman, U.S. Pat. No. 5,536,743.

Compositions containing metronidazole for treatment of dermatologic disorders are available in both cream and gel forms. One commercially available metronidazole cream product, NORITATE™ (Dermik Laboratories, Inc., Collegeville, Pa. 19426 USA) contains 1% metronidazole and is directed to be applied once daily to affected areas. A commercially available metronidazole gel product, METROGEL® (Galderma Laboratories, Inc. Fort Worth, Tex., 76133 USA), contains 0.75% and is applied twice daily to affected areas.

For the treatment of many dermatologic and mucosal disorders, it is often preferable to use a gel formulation rather than a cream or an ointment. Creams (typically oil in water emulsions) and ointments (typically petroleum jelly based compositions) are often comedogenic, acnegenic, or not cosmetically appealing to patients.

The oil-based cream and ointment metronidazole formulations have an advantage over gel-based formulations in that oil-based formulations may contain a concentration of metronidazole of 1%. Aqueous-based gel compositions are limited to a concentration of metronidazole of 0.75% because of the poor solubility of metronidazole in water. Because of this, metronidazole gel products must be applied on at least a twice daily basis.

Cyclodextrins, especially β-cyclodextrins, have been shown to enhance the solubility of various drugs in aqueous solutions. Yie W. Chien, Journal of Parenteral Science and Technology, 38(1):32–36 (January 1984), describes the increase in water solubility of MTZ by addition of niacinamide. The Chien article is incorporated herein by reference. The cyclodextrins and niacinamide enhance solubility by formation of a "cage" structure having an external hydrophilic face and an internal hydrophobic face.

A drug, such as metronidazole, is partially or completely enclosed within this cage structure, thereby increasing the solubility of the drug. Beta-cyclodextrin, ("BCD") and various derivatives of BCD, including methylated and ethylated cyclodextrins, hydroxypropyl-β-cyclodextrin (referred to in this application as "HPCD"), and hydroxyethyl-β-cyclodextrin have been used to increase solubility of drugs.

Several authors have described the use of β-cyclodextrin in combination with metronidazole. Kata and Antal, Acta Pharmaceutica Hungarica, 54:116–122 (1984), disclose a marked increase in the rate of dissolution of metronidazole when dissolved in a solution containing BCD. The stability of the BCD/metronidazole solutions is not addressed. Also, use of β-cyclodextrin ("BCD") is limited however due to its relatively low solubility in water and toxicity when administered internally.

Publications by other authors concerning the use of derivatives of BCD show that any increase in the solubility of a drug that is obtained by combining with the BCD derivative cannot be extrapolated to other drugs. Also, any increase in the solubility of a drug due to any particular derivative of BCD cannot be extrapolated to another derivative of BCD.

Pitha, U.S. Pat. No. 4,596,795, discloses that the solubility of the sex steroids testosterone, progesterone, and estradiol was greatly improved with HPCD and with poly-beta cyclodextrin, which are highly soluble in water, easily dissolving to 40% w/w solutions. However, solubility of the sex steroids was only marginally improved with BCD, which forms saturated aqueous solutions at about 2% w/w.

Stella, PCT application International Publication WO 91/11172, discloses that digoxin is five times more water soluble when combined with BCD than when it is combined with HPCD. Stella also discloses that testosterone and phenytoin are more water soluble when combined with BCD than when combined with HPCD.

Bodor, EP 0335545 B1, discloses that a 50% w/w concentration of HPCD increases the water solubility of several drugs, including chlordiazepoxide, dexamethasone, diazepam, estradiol, ethynylestradiol, medazepam, methotrexate, norethindrone, norethindrone acetate, norgestrel, oxazepam, phenytoin, and all-trans-retinol. Bodor further discloses that, in order to obtain a particular dissolved concentration of an estradiol compound, the concentration of HPCD must be maintained above 20% because, at levels less than this, the solutions are unstable and precipitation occurs.

Muller, WO 85/02767, discloses that certain hydroxyalkylated derivatives of BCD, including hydroxyethyl, hydroxypropyl, and dihydroxypropyl BCD, increase the solubility of various drugs in aqueous solution. Muller discloses that 10% HPCD increases the solubility of indomethacin, digitoxin, progesterone, dexamethasone, hydrocortisone, and diazepam in a phosphate buffer aqueous solution. No information was provided concerning the stability of these solutions. Muller further discloses that solutions of 4% hydroxypropyl-methyl-BCD increased the solubility of several compounds, including several imidazole compounds, and that solutions of 7% hydroxyethyl-BCD increased the solubility of indomethacin. The drugs dissolved in these solutions were found to be chemically stable, as determined by high pressure liquid chromatography. Muller does not address the problem of physical stability over time as described in Bodor regarding solutions containing less than 50% HPCD.

SUMMARY OF THE INVENTION

It has been surprisingly discovered that physically stable aqueous solutions of higher than 0.75% metronidazole (MTZ) w/w may be obtained by combining in the solution an amount of hydroxypropyl-betacyclodextrin (HPCD), preferably at a level less than 20%. It has further been surprisingly discovered that the combination of HPCD and niacinamide has a synergistic effect in increasing the solubility of MTZ in water. These discoveries permit the production of aqueous MTZ solutions, including gel solutions, at levels of 1% MTZ or higher. At such levels, MTZ may be effectively used as a topical medicament when applied only once daily.

In one embodiment, the invention is an aqueous solution having a concentration of MTZ higher than 0.75% w/w. The aqueous solution contains HPCD, or a combination of HPCD and niacinamide. Preferably, the level of HPCD is less than 20% and the concentration of niacinamide is less than that which, without HPCD, increases the concentration of MTZ to the level of that in the aqueous solution. Preferably, the solution is substantially free of MTZ solubility-enhancing agents other than HPCD or other than HPCD in combination with niacinamide. Preferably, the solution is an aqueous gel.

In another embodiment, the invention is a method for the manufacture of an aqueous solution of MTZ having a concentration greater than 0.75%. The method includes combining MTZ and HPCD, or MTZ, HPCD, and niacinamide, in a water based solution wherein the concentration of the final aqueous solution of MTZ is higher than 0.75%. Preferably, the level of HPCD is less than 20%, and the concentration of niacinamide is less than that which, by itself, increases the concentration of MTZ to the level of that in the aqueous solution. Preferably, a gelling agent is further combined with the MTZ and HPCD or with the MTZ, HPCD, and niacinamide.

In another embodiment, the invention is a method for the treatment of a dermatologic or mucosal disorder. The method includes topically applying to affected areas an aqueous solution of MTZ and HPCD, or of MTZ, HPCD, and niacinamide, in which the concentration of MTZ is higher than 0.75%. Preferably, the concentration of HPCD is less than 20%, and the concentration of niacinamide is less than that which, by itself, increases the concentration of MTZ to the level of that in the aqueous solution. Preferably, the aqueous solution is a gel.

In another embodiment, the invention is a kit for the treatment of a dermatologic or mucosal disorder. The kit of the invention includes a container that contains an aqueous solution of MTZ and HPCD or of MTZ and HPCD and niacinamide, in which the concentration of MTZ is higher than 0.75%, and instructions for topically applying the aqueous solution once daily to affected areas. Preferably, the concentration of HPCD is less than 20%, and the concentration of niacinamide is less than that which, by itself, increases the aqueous solubility of MTZ to the level of MTZ in the aqueous solution.

DETAILED DESCRIPTION OF THE INVENTION

Figure 1:
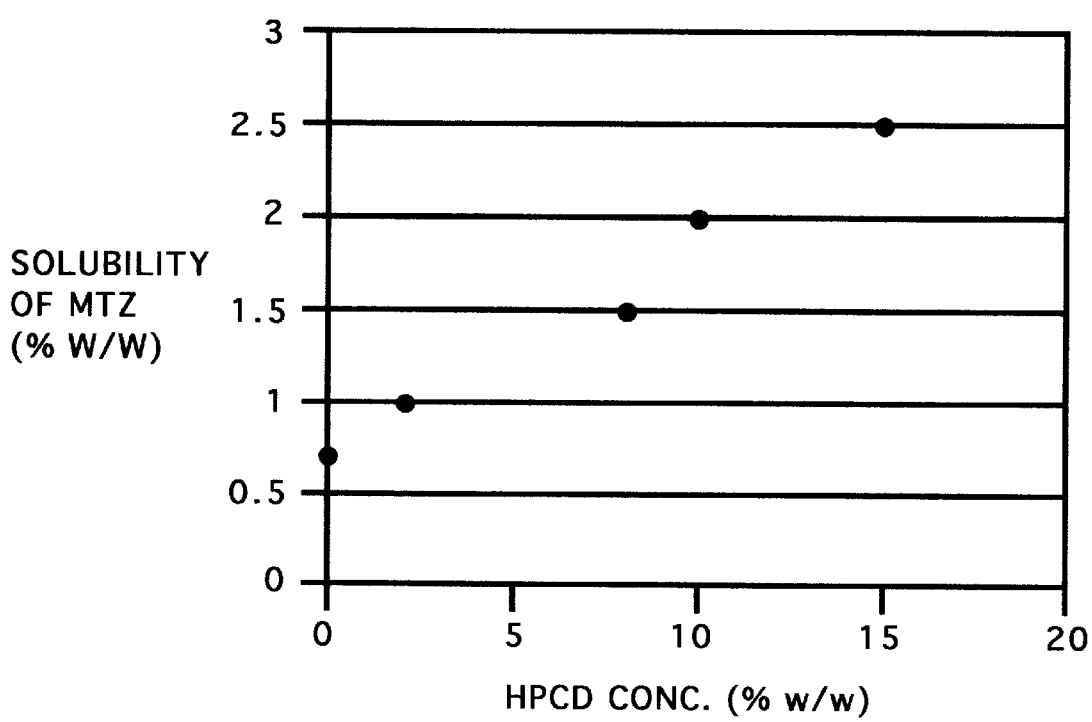
FIG. 1 is a graph showing the concentration of MTZ in aqueous solution as a function of the concentration of HPCD.

It has been unexpectedly discovered that stable aqueous solutions of metronidazole (MTZ) of greater than 0.75% w/w are able to be obtained by including hydroxypropyl-betacyclodextrin (HPCD), preferably at a level of less than 20% w/w in the solution, or by including HPCD and niacinamide in the solution, wherein HPCD is preferably less than 20% w/w of the solution and niacinamide is at a level less than the level at which it by itself raises the solubility of MTZ to the level in the solution.

As used in this specification, the term "stable" refers to physical, rather than chemical, stability. The present invention overcomes the problems noted in the prior art of precipitation of solutes at levels of HPCD of less than 20%. See Bodor, EP 0335545B1, incorporated herein by reference, at page 52. In accordance with the invention, the metronidazole solutions of the invention are physically stable, that is substantially no precipitation of metronidazole from solution, when stored at refrigerated temperatures of 5° C. for 14 days or longer.

The physically stable aqueous solutions of metronidazole at concentrations greater than 0.75% are obtained without the substantial presence of water-miscible organic solvents, such as propylene glycol, which may be irritating to intact or damaged skin or mucosal surfaces. The elimination of these organic solvents provides a therapeutic solution that has decreased potential for irritation and makes the solutions especially good for treating topical dermatologic conditions, such as acne rosacea, that may be worsened by irritating chemicals present in a therapeutic formulation. However, if desired, such organic solvents may be included in the solution, up to a concentration of about 10%. In a most preferred embodiment, the aqueous solutions are substantially free of solvents for MTZ other than water.

The stable aqueous MTZ solutions of the invention have a concentration of MTZ greater than 0.75% w/w. Preferably, the concentration of MTZ in the solution of the invention is about 1.0%. In accordance with the invention, the concentration of MTZ in aqueous solution may be even higher, such as 1.25%, 1.5%, 2.0%, or 2.5%, or more. At a level of 1% or higher of MTZ, the aqueous solution may be effectively used therapeutically as a topical formulation on a once daily regimen. Presently available topical MTZ therapeutic aqueous solutions must be applied at least twice daily.

The solution is preferably in the form of a gel. Therefore, the aqueous MTZ solution preferably contains a gelling agent. Any gelling agent that is water-dispersible and forms an aqueous gel of substantially uniform consistency is suitable for use in the solution of the invention so long as the gelling agent does not substantially interfere with the water solubility of MTZ or with the therapeutic efficacy of the solution. "Substantially interfere" means that the inclusion of the gelling agent decreases the solubility of MTZ to 0.75% w/w or less in aqueous solution or that it necessitates the administration of the topical solution to be more than once per day. A preferred gelling agent is hydroxycellulose (NATROSOL™, Hercules Inc., Wilmington, Del., USA).

The level of HPCD in the solution may be varied depending upon the desired dissolved concentration of MTZ. In general, it is preferable to use as low a concentration of HPCD as possible to obtain the desired concentration of MTZ because the presence of HPCD may be irritating to certain intact and diseased skin and mucosal surfaces. In accordance with the invention, the concentration of HPCD in aqueous solution may be between 0.5% and 20%, or higher. Preferably, the concentration of HPCD in the solution is no more than about 4% or 5% w/w. Most preferably, the concentration of HPCD is between 1% and 2%.

The solutions, especially in gel formulation, have been found to be non-tacky, fast-drying, and cosmetically elegant. The solutions, including the gel formulations, are physically stable at 5° C. refrigerator or room temperature conditions. No crystal formation or precipitation is observed after one month or more of storage.

It is preferred that the aqueous solution of the invention be substantially free of compounds other than MTZ having a water-solubility which is increased by the presence of HPCD. These other compounds may act as competitors for the sequestration sites within the HPCD cage structure and reduce the MTZ solubility enhancement of the HPCD. Multiple solutes that are increased in solubility by HPCD may be utilized in the solutions so long as the level of HPCD in the solution is sufficiently high to result in the desired dissolved concentration of MTZ, even in the presence of the competitor solute.

In one embodiment of the invention, the amount of HPCD is reduced to a level below that which enhances the solubilization of MTZ to the level desired, and niacinamide is included in the solution at a level that permits the desired concentration of MTZ in aqueous solution to be attained. For example, if a stable 1% MTZ aqueous solution is desired, less than 5.0% HPCD may be used and an amount of niacinamide may be combined in the solution to bring the solubility of MTZ to 1%. The amount of niacinamide to be combined in the solution is less than that which, without the presence of HPCD in the solution, can enhance the solubility of MTZ sufficiently to obtain a 1% solution of MTZ, or whatever level of MTZ is desired. In accordance with this embodiment of the invention, the amount of HPCD % w/w in the solution is preferably at least equal to that of niacinamide. Most preferably, the concentration of HPCD in the solution is at least 1.5 times that of niacinamide.

The aqueous solutions, including the aqueous gels, of the invention may be made in any way that results in a stable MTZ concentration of greater than 0.75%, preferably of 1.0% or higher. Preferably, the solubility enhancer HPCD, or HPCD and niacinamide, and the MTZ are combined in water, or a water-based solution, before the addition of a gelling agent, or at least before gelling of the solution occurs. Preferably, the HPCD, or HPCD plus niacinamide, are dissolved in water before addition of the MTZ.

In a preferred method of manufacture of the aqueous solution of the invention, an aqueous solution of HPCD is prepared having the desired concentration of HPCD. Alternatively, an HPCD and niacinamide aqueous solution is prepared, wherein the levels of HPCD and niacinamide are as described above. Metronidazole is then added to the solution. The amount of metronidazole added to the solution may be an amount calculated to provide the desired concentration of MTZ or it may be an excess amount of MTZ. The solution is preferably stirred or agitated at an elevated temperature and then permitted to cool to room or refrigerator temperature. A gelling agent, if desired, is preferably added at any time after the addition of MTZ to the solution. Most preferably, the gelling agent is added to the solution after the agitation of the solution, during the cooling of the solution, or following cooling of the solution.

The solutions of the invention, including gels, may be used for the topical treatment of dermatologic or mucosal disorders that are responsive to therapy with metronidazole. In accordance with the method of treatment of the invention, a stable aqueous solution containing metronidazole at a concentration higher than 0.75% w/w, preferably about 1% or higher, is topically applied to skin or mucosal surfaces in need of such therapy. The applied solution preferably contains HPCD, as described above, or a combination of HPCD and niacinamide, as described above.

The therapeutic method of the invention may be used to treat any disorder that is responsive, or potentially responsive, to metronidazole therapy. Examples of disorders that are suitably treated in accordance with the invention include inflammatory lesions on the skin, oral mucosa, or vaginal mucosa, diabetic foot ulcers, and certain infectious diseases that may be treated topically. In a preferred embodiment, the method of the invention is used to treat acne rosacea.

At concentrations of about 1% or higher, the application of the metronidazole solution is preferably only once daily. The solution is applied on a daily basis, one or more times per day, for a time sufficient to produce an amelioration or a cure of the disorder. In certain chronic disorders, the solution may be applied once or more times daily for a prolonged period to prevent worsening of the disorder.

Figure 2:
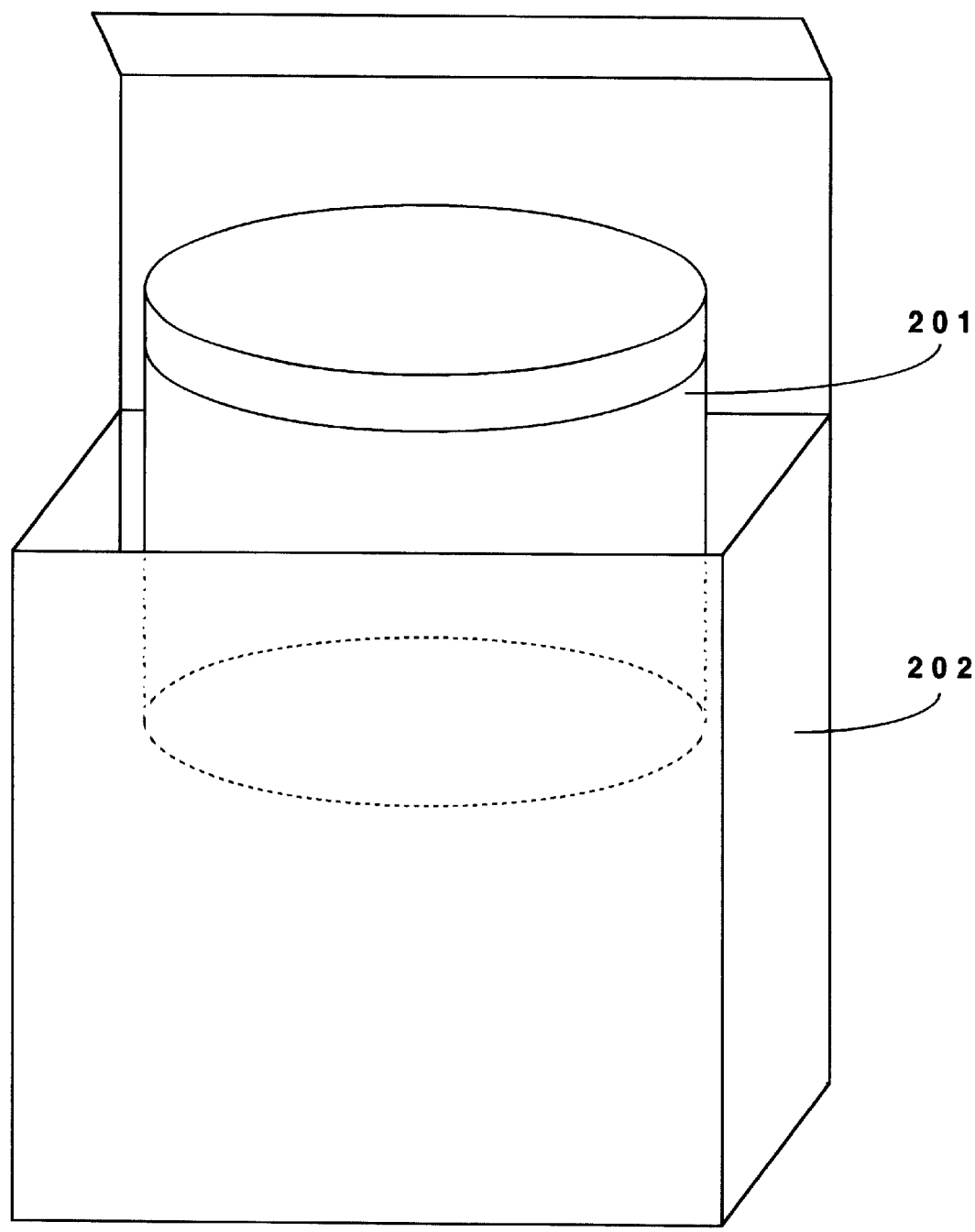
FIG. 2 shows a diagrammatic representation of a preferred embodiment of the kit of the invention.

In another embodiment of the invention, a kit (FIG. 2) is provided for the topical treatment of skin or mucosal disorders. The kit contains a jar 201 or other container suitable for holding an aqueous metronidazole solution as described herein, and instructions (not illustrated) for applying the solution topically to affected areas of the skin or mucosal surface. Preferably, the metronidazole solution has a concentration of metronidazole of about 1% or higher and the instructions call for applying the metronidazole solution to affected areas once daily. The jar 201 is preferably packaged within a box 202, upon which additional information, such as instructions, may be written.

The following non-limiting examples provide a further description of the invention.

EXAMPLE 1

Preparation of Aqueous Metronidazole Solutions

Various solutions of hydroxypropyl-beta-cyclodextrin (HPCD) were prepared by combining a quantity of HPCD in water to yield the desired concentration of HPCD between 1% w/w and 15% w/w. To each HPCD solution, an excess amount of metronidazole was added. The solutions were placed in a shaker bath at about 60° C. for about 2 hours or more. After shaking, the samples were permitted to cool to room temperature and were stored at 5° C. A gelling agent was then added to the samples to form an aqueous metronidazole gel. The resultant concentrations of metronidazole in the solutions are shown in Table 1.

In accordance with the invention, stable aqueous metronidazole at the following concentrations may be obtained with the following concentrations of HPCD as shown in Table 1 and FIG. 1.

TABLE 1

| Concentration of HPCD (% w/w) | 0.0 | 2.0 | 8.0 | 10.0 | 15.0 |
|---|---|---|---|---|---|
| Solubility* of MTZ (% w/w) | 0.7 | 1.0 | 1.5 | 2.0 | 2.5 |

*Solubility of metronidazole in aqueous solutions with different HPCD concentrations estimated by solution stability following 1-day storage at room temperature followed by 1-day storage at 5° C.

EXAMPLE 2

1.0% Metronidazole Gel Solution

A stable 1.0% aqueous gel was prepared in accordance with Example 1 with the following components:

| | | |
|---|---|---|
| Metronidazole, USP | 1.00% | Active Ingredient |
| Hydroxypropyl-beta-cyclodextrin | 5.00% | Solubility Agent |
| Methylparaben, NF | 0.15% | Antimicrobial |
| Propylparaben, NF | 0.03% | Antimicrobial |
| Glycerin, USP | 5.00% | Humectant |
| Hydroxyethylcellulose, NF | 1.50% | Gelling Agent |

-continued

| | | |
|---|---|---|
| Disodium Edetate, USP | 0.05% | Chelating Agent |
| Purified Water, USP | QS 100% | Solvent/Vehicle. |

EXAMPLE 3

1.25% Metronidazole Gel Solution

A stable 1.25% aqueous gel was prepared in accordance with Example 1 with the following components:

| | | |
|---|---|---|
| Metronidazole, USP | 1.25% | Active Ingredient |
| Hydroxypropyl-beta-cyclodextrin | 12.00% | Solubility Agent |
| Methylparaben, NF | 0.15% | Antimicrobial |
| Propylparaben, NF | 0.03% | Antimicrobial |
| Glycerin, USP | 5.00% | Humectant |
| Hydroxyethylcellulose, NF | 1.50% | Gelling Agent |
| Disodium Edetate, USP | 0.05% | Chelating Agent |
| Purified Water, USP | QS 100% | Solvent/Vehicle. |

EXAMPLE 4

1.0% Metronidazole Gel Solution

A stable 1.0% aqueous gel was prepared in accordance with the following components:

| | | |
|---|---|---|
| Metronidazole, USP | 1.0% | Active Ingredient |
| Hydroxypropyl-beta-cyclodextrin | 5.00% | Solubility Agent |
| Methylparaben, NF | 0.15% | Antimicrobial |
| Propylparaben, NF | 0.03% | Antimicrobial |
| Hydroxyethylcellulose, NF | 1.25% | Gelling Agent |
| Disodium Edetate, USP | 0.05% | Chelating Agent |
| Purified Water, USP | QS 100% | Solvent/Vehicle. |

The solutions of Examples 2 to 4 were shown to be physically stable (as determined by pH, viscosity, and appearance), and chemically stable for the periods and at the different temperatures summarized in Table 2.

TABLE 2

| Sample | 5° C. | 25° C. | 40° C. |
|---|---|---|---|
| Example 2 | 3 months | 12 months | 6 months |
| Example 3 | 3 months | 3 months | 6 months |
| Example 4 | 3 months | 12 months | 6 months |

EXAMPLE 5

Stability of Metronidazole Aqueous Solutions

Several metronidazole solutions were prepared with various derivatives of cyclodextrin at varying concentrations. The solutions were stored at room temperature and were observed for the presence of precipitation, which would indicate that the solutions were not physically stable. Solutions of MTZ and HPCD were found to be stable, whereas solutions of identical metronidazole concentration made with other derivatives of cyclodextrin were found to be unstable. The solutions that were stable at room temperature were then subjected to refrigerator temperature, 5° C., a more rigorous test of physical stability, to determine their physical stability at this lower temperature. The data is shown in Table 3.

TABLE 3

Stability of metronidazole/cyclodextrin solutions

| Cyclodextrins | MTZ % w/w | Room Temp. | 5° C. |
|---|---|---|---|
| 5% HPCD | 1.0 | None | None for 30 days |
| 2% beta-cyclodextrin | 1.0 | 1 day | — |
| 2.25% beta-cyclodextrin | 1.0 | 1 day | — |
| 5% alpha-cyclodextrin | 1.0 | None | None for 5 days |
| 5% gamma-cyclodextrin | 1.0 | 2 days | — |
| 10% HPCD | 1.5 | None | None for 10 days |
| 10% gamma-cyclodextrin | 1.5 | 1 day | — |
| 10% alpha-cyclodextrin | 1.5 | 1 day | — |
| 2.25% beta-cyclodextrin | 1.5 | 1 day | — |

As shown in Table 3, 1% metronidazole solutions containing 5% HPCD were more physically stable than those containing the same amount of gamma-cyclodextrin or maximally dissolvable concentrations of beta-cyclodextrin. MTZ solutions with alpha-cyclodextrin were also stable at room temperature and for five days of refrigeration. At 1.5% concentration of MTZ, 10% solutions of the cyclodextrin derivatives other than HPCD were unstable at room temperature, with precipitation of MTZ occurring at one day at room temperature. In contrast, the 1.5% MTZ solution containing 10% HPCD was determined to be stable at room temperature and at refrigeration for at least 10 days.

EXAMPLE 6

In vitro Release Study of Topical Metronidazole Preparations

Table 4 shows the composition of four samples of metronidazole solutions.

TABLE 4

| Components | Sample A | Sample B | Sample C | Sample D |
|---|---|---|---|---|
| Metronidazole, USP | 1.00 | 1.00 | 0.75 | 0.75 |
| HPCD | 5.00 | 5.00 | 5.00 | 0 |
| Methylparaben, NF | 0.15 | 0.15 | 0.15 | 0.15 |
| Propylparaben, NF | 0.03 | 0.03 | 0.03 | 0.03 |
| Edetate Sodium, USP | 0.05 | 0.05 | 0.05 | 0.05 |
| Hydroxyethylcellulose 250HHX, NF | 1.25 | 1.25 | 1.25 | 1.25 |
| Glycerin, USP | 5.00 | 0 | 5.00 | 5.00 |
| Purified Water, USP | 87.52 | 92.52 | 87.77 | 92.77 |

The release pattern of metronidazole was evaluated for each of the four samples described in Table 4. The release pattern was also evaluated for a commercial 1% metronidazole cream, NORITATE™ and for a commercial 0.75% metronidazole gel, METROGEL™.

The release study was conducted with Franz Diffusion Cells using Spectrapor™ membrane (available from Spectrum Medical Industries, Inc., Los Angeles, Calif. 90054) having a molecular weight cutoff of between 12,000 and 14,000. The membrane had been soaked for one hour in a buffer having a pH of 5.5. The temperature of the Franz Diffusion Cell system was maintained at 32° C. The volume of the sample was replaced each time with fresh solution. The samples were analyzed for metronidazole by flow injection analysis monitored at 319 nm.

Release rate data, expressed as mg/cm$^2$ per unit time was identical for Sample A and the commercial metronidazole cream, each of which contains 1% metronidazole. Sample B, which was identical to Sample A except that Sample B contains no glycerin, had a slightly lower release rate than Sample A and the commercial cream. However, the difference appeared to be insignificant.

The release pattern of 0.75% metronidazole formulations were nearly identical to that of the 1.0% formulations up to 60 minutes. After that time, the 0.75% formulations had a decreased release rate compared to the 1.0% formulations, most likely due to more rapid depletion of metronidazole from the less concentrated formulations.

EXAMPLE 7

Solubility of Imidazole Compounds in Hydroxypropyl and Hydroxyethyl Beta-cyclodextrin Six sample solutions were prepared as described in Example 1 except as follows. Two groups of three sample solutions each were prepared. In one group of three samples, the solubility enhancer was 4% hydroxypropyl-betacyclodextrin (HPCD). In the other group of three samples, the solubility enhancer was 4% hydroxyethyl-betacyclodextrin (HECD). Into the three samples in each group an excess amount of one of the imidazole compounds metronidazole, ketoconazole, or itraconazole, respectively, was added. The solubility of each of the samples was determined as shown in Table 5 and was compared to the solubility of the imidazole in purified water without a solubility enhancer.

TABLE 5

| | Solubility of Imidazole Compounds in Derivatives of Betacyclodextrin | | |
|---|---|---|---|
| Imidazole | Purified Water % w/w solubility | 4% HPCD % w/w solubility | 4% HECD % w/w solubility |
| Metronidazole | 0.9–1.0 | 1.1–1.2 | 1.2–1.3 |
| Ketoconazole | less than 0.01 | 0.01–0.03 | 0.03–0.05 |
| Itraconazole | less than 0.01 | less than 0.01 | less than 0.01 |

As shown in Table 5, the solubility of metronidazole was increased with the addition of 4% HPCD to purified water by about 20% and with 4% HECD by about 30%. The solubility of ketoconazole was increased about 100 and 300 per cent, respectively. For itraconazole, the increase in solubility was not measurable for either HPCD or HECD. In addition, the 4% HECD and metronidazole solution became yellow upon addition of the metronidazole, suggesting that this solution was unstable. In contrast, the 4% HPCD and metronidazole solution remained clear and colorless.

The data in Table 5 shows that the increase in solubility of a drug due to its interaction with a particular derivative of betacyclodextrin cannot be predicted based upon the increase in solubility obtained with a different, even a closely related, derivative of betacyclodextrin. The data in Table 5 further shows that the increase in solubility of a drug due to its interaction with a derivative of betacyclodextrin cannot be predicted based upon the increase in solubility of a different drug, even a closely related drug, with that betacyclodextrin derivative.

EXAMPLE 8

Solubility of Metronidazone in an Aqueous Solution Containing Hydroxypropyl-betacyclodextrin and Niacinamide HPCD and niacinamide solutions were prepared and the concentrations of each to obtain a stable 1% metronidazole solution at 5° C. were determined as 5% and 3%, respectively. Then various combinations of HPCD and niacinamide concentrations in aqueous solution containing 1% metronidazole were prepared as in Example 1.

In the combination solutions, HPCD concentration was in the range of 0% to 5% and the concentration range of niacinamide was 0% to 3%. The solutions were kept at room temperature and 5° C. for a week to assess the maintenance of the dissolved state.

For solubilization effects of HPCD and niacinamide combinations, the concentrations of HPCD and niacinamide were determined in 1% metronidazole solutions, which were clear with no precipitate. Metronidazole solubility was visually determined after a week storage. In order to evaluate the solubilization capacity of the HPCD and niacinamide combinations, the niacinamide concentration required to make 1.5% metronidazole in 5% HPCD solution was determined by keeping the solution at 5° C. for 1 week.

When HPCD was used as a solubilizer, 5% HPCD was required to make a stable 1% metronidazole aqueous solution. When the concentration of HPCD was reduced to 4% or less, aqueous solutions containing 1% metronidazole showed a precipitation formation when kept at 5° C. for 1 week. When niacinamide was used as a solubilizer, 3% niacinamide was required to make 1% metronidazole aqueous solution. When the concentration of niacinamide was reduced to 2% or less, aqueous solutions containing 1% metronidazole showed a precipitation formation when kept at 5° C. for 1 week.

When HPCD and niacinamide were combined in 1% metronidazole solution, it was found that a stable 1% MTZ solution could be obtained with concentrations of HPCD and niacinamide of 1.0% and 0.5%, respectively. The combination of HPCD and niacinamide results in a synergistic effect on metronidazole solubilization.

The amounts (% w/w) required to obtain a clear stable solution of 1% Metronidazole in water for HPCD and niacinamide were 5% and 3% respectively. However, when HPCD and niacinamide were added as a combination solubility enhancer, the respective concentrations required to obtain a clear stable 1% metronidazole solution were 1% and 0.5%, respectively.

Metronidazole was added to a 1% metronidazole solution containing 5% HPCD until the concentration reached 1.5%. The solution then showed a precipitate at room temperature. The addition of niacinamide to a concentration of 6% permitted the excess metronidazole to dissolve to reestablish a 1.5% metronidazole solution. This solution stayed clear with no precipitate for 1 week at 5° C.

These results demonstrate that the combination of HPCD and niacinamide produces a synergistic effect in metronidazole solubilization. A clear 1% metronidazole aqueous solution required either 5% HPCD or 3% niacinamide when either solubilizer was used alone. When HPCD and niacinamide were combined, a 1% metronidazole aqueous solution required only 1% HPCD and 0.5% niacinamide. A clear 1.5% metronidazole aqueous solution could be prepared by combining 5% HPCD and 6% niacinamide as a combined solubilizer system.

EXAMPLE 9

1.0% Metronidazole Gel Solution With HPCD and Niacinamide

A stable 1.0% aqueous gel was prepared in accordance with the following components:

| | | |
|---|---|---|
| Metronidazole, USP | 1.0% | Active Ingredient |
| Hydroxypropyl-beta-cyclodextrin | 1.0% | Solubility Agent |
| Niacinamide | 1.0% | Solubility Agent |
| Methylparaben, NF | 0.15% | Antimicrobial |
| Propylparaben, NF | 0.03% | Antimicrobial |
| Hydroxyethylcellulose, NF | 1.25% | Gelling Agent |
| Disodium Edetate, USP | 0.05% | Chelating Agent |
| Purified Water, USP | QS 100% | Solvent/Vehicle. |

EXAMPLE 10

1.5% Metronidazole Gel Solution With HPCD and Niacinamide

A stable 1.5% aqueous gel was prepared in accordance with the following components:

| | | |
|---|---|---|
| Metronidazole, USP | 1.5% | Active Ingredient |
| Hydroxypropyl-beta-cyclodextrin | 5.0% | Solubility Agent |
| Niacinamide | 6.0% | Solubility Agent |
| Methylparaben, NF | 0.15% | Antimicrobial |
| Propylparaben, NF | 0.03% | Antimicrobial |
| Hydroxyethylcellulose, NF | 1.25% | Gelling Agent |
| Disodium Edetate, USP | 0.05% | Chelating Agent |
| Purified Water, USP | QS 100% | Solvent/Vehicle. |

EXAMPLE 11

1.5% Metronidazole Gel Solution With HPCD

A stable 1.5% aqueous gel was prepared in accordance with the following components:

| | | |
|---|---|---|
| Metronidazole, USP | 1.5% | Active Ingredient |
| Hydroxypropyl-beta-cyclodextrin | 15.0% | Solubility Agent |
| Methylparaben, NF | 0.15% | Antimicrobial |
| Propylparaben, NF | 0.03% | Antimicrobial |
| Hydroxyethylcellulose, NF | 1.25% | Gelling Agent |
| Disodium Edetate, USP | 0.05% | Chelating Agent |
| Purified Water, USP | QS 100% | Solvent/Vehicle. |

Various modifications of the above described invention will be evident to those skilled in the art. It is intended that such modifications are included within the scope of the following claims.

What is claimed is:

1. An aqueous solution comprising hydroxypropyl-betacyclodextrin (HPCD), niacinamide, and metronidazole.

2. The aqueous solution of claim 1 wherein the concentration of metronidazole in solution is higher than 0.75%.

3. The aqueous solution of claim 2 wherein the concentration of metronidazole is about 1% or higher.

4. The aqueous solution of claim 1 wherein the concentration of each of the HPCD and the niacinamide present in the solution is below that which is sufficient, in the absence of the other, to obtain the concentration of metronidazole that is present in the solution.

5. The aqueous solution of claim 1 wherein the concentration of metronidazole is about 1%, the concentration of HPCD is about 1%, and the concentration of niacinamide is about 0.5 to 1 percent.

6. The aqueous solution of claim 1 wherein the concentration of metronidazole is about 1.5%, the concentration of HPCD is about 5%, and the concentration of niacinamide is about 6%.

7. The aqueous solution of claim 1 which is substantially free of metronidazole solubility-enhancing agents other than HPCD and niacinamide.

8. The aqueous solution of claim 1 which is substantially free of organic solvents.

9. The aqueous solution of claim 1 which further comprises a gelling agent.

10. A method for making an aqueous solution of metronidazole comprising combining hydroxypropyl-betacyclodextrin (HPCD), niacinamide, and metronidazole in water.

11. A The method of claim 10 wherein the metronidazole is added to the water following the dissolution of the HPCD and the niacinamide in the water.

12. The method of claim 10 which further comprises, after the combination of HPCD, niacinamide, and metronidazole in the water, adding a gelling agent.

13. The method of claim 10 wherein the amount of each of the HPCD and the niacinamide that is combined in the water is below that which, in the absence of the other, is sufficient to obtain the concentration of metronidazole that is obtained upon combining the metronidazole in the water containing both the HPCD and the niacinamide.

14. An aqueous solution produced by the method of claim 10.

15. An aqueous solution produced by the method of claim 11.

16. An aqueous solution produced by the method of claim 12.

17. A method for the treatment of a dermatologic or mucosal disorder comprising topically applying an effective amount of aqueous solution of metronidazole having a concentration higher than 0.75% w/w to the site of the disorder and permitting the metronidazole to treat the disorder, wherein the solution further comprises hydroxypropyl-betacyclodextrin and niacinamide.

18. The method of claim 17 wherein the application is once daily.

19. The method of claim 17 wherein the concentration of metronidazole is about 1% or higher.

20. The method of claim 17 wherein the disorder is acne rosacea.

21. A kit for the topical treatment of dermatologic or mucosal disorders comprising a container and an aqueous solution of metronidazole within the container, wherein the solution further comprises hydroxypropyl-betacyclodextrin (HPBD) and niacinamide.

22. The kit of claim 21 wherein the concentration of metronidazole in the solution is 0.75% or higher.

23. The kit of claim 22 wherein the concentration of metronidazole in the solution is about 1% or higher.

24. The kit of claim 23 wherein the concentration of metronidazole is about 1%, the concentration of HPBD is about 1%, and the concentration of niacinamide is about 0.5 to 1%.

25. The kit of claim 23 wherein the concentration of metronidazole is about 1.5%, the concentration of HPBD is about 5%, and the concentration of niacinamide is about 6%.

26. The kit of claim 23 which further comprises written instructions to apply the solution to affected areas once daily.

27. The aqueous solution of claim 1 wherein the concentration of HPCD is equal to or greater than the concentration of niacinamide.

28. The aqueous solution of claim 27 wherein the concentration of HPCD is equal to or greater than 1.5 times the concentration of niacinamide.

* * * * *